United States Patent [19]

Distler et al.

[11] 4,049,968

[45] Sept. 20, 1977

[54] TOMOGRAPHIC X-RAY APPARATUS FOR PRODUCING TOMOGRAPHIC IMAGES

[75] Inventors: Walter Distler, Erlangen; Roderich Zink, Herzogenaurach;. Gerhard Linke, Erlangen-Frauenaurach, all of Germany

[73] Assignee: Siemens Aktiengesellschaft, Berlin & Munich, Germany

[21] Appl. No.: 601,706

[22] Filed: Aug. 4, 1975

[30] Foreign Application Priority Data

Aug. 5, 1974 Germany .............................. 2437710

[51] Int. Cl.² ............................................ G03B 41/16
[52] U.S. Cl. ................................ 250/445 T; 250/510
[58] Field of Search .................. 250/439, 445 T, 451, 250/456, 510

[56] References Cited

U.S. PATENT DOCUMENTS 3,867,634  2/1975  Hounsfield ....................... 250/445 T

*Primary Examiner*—Craig E. Church
*Attorney, Agent, or Firm*—Hill, Gross, Simpson, Van Santen, Steadman, Chiara & Simpson

[57] ABSTRACT

A tomographic X-ray apparatus for the producing of transverse laminographic or tomographic images, constituted of an X-ray measuring arrangement having an X-ray source which generates an X-ray beam, whose cross-sectional expanse or spread perpendicular to the X-rayed layer is equal to the layer thickness, and in parallel to the layer is equal to the layer thickness or is lesser than the latter; and including a radiation receiver which measures the radiation intensity behind the object at successive equidistant points, as well as a drive installation for the measuring arrangement, consisting of a pivot mounting for producing rotary movements of the X-ray measuring arrangement through small equidistant angular increments about a rotational axis which is approximately coincident with the symmetrical longitudinal axis of the exposure object; as well as a slide carriage located on the pivot mounting for producing a linear scanning movement (scanning lift) of the X-ray measuring arrangement perpendicular to the direction of the central X-ray beam over the entire object expanse in an alternating sequence with each incremental rotary movement; and including a holding installation for the exposure object in the X-ray path consisting of a rectangular or box-shaped, in the radiation direction homogeneous and uniformly absorbent, compensating body of tissue-equivalent material encompassing the exposure object, which is fixedly connected with the pivot mounting of the X-ray measuring arrangement, whose extent in the direction of the scanning movement is equal to or larger than the scanning lift, and which possesses an elastic contouring body resting opposite the rotary compensating body, and which is closely located against the surface of the exposure object after the introduction of the latter into the compensating body.

3 Claims, 4 Drawing Figures

TOMOGRAPHIC X-RAY APPARATUS FOR PRODUCING TOMOGRAPHIC IMAGES

FIELD OF THE INVENTION

The present invention relates to a tomographic X-ray apparatus for the producing of transverse laminographic or tomographic images, constituted of an X-ray measuring arrangement having an X-ray source which generates an X-ray beam, whose cross-sectional expanse or spread perpendicular to the X-rayed layer is equal to the layer thickness, and in parallel to the layer is equal to the layer thickness or is less than the latter; and including a radiation receiver which measures the radiation intensity behind the object at successive equidistant points, as well as a drive installation for the measuring arrangement, consisting of a pivot mounting for producing rotary movements of the X-ray measuring arrangement through small equidistant angular increments about a rotational axis which is approximately coincident with the symmetrical longitudinal axis of the exposure object; aswell as a slide carriage located on the pivot mounting for producing a linear scanning movement (scanning lift) of the X-ray measuring arrangement perpendicular to the direction of the central X-ray beam over the entire object expanse in an alternating sequence with each incremental rotary movement; and including a holding installation for the exposure object in the X-ray path consisting of a rectangular or box-shaped, in the radiation direction homogeneous and uniformly absorbent, compensating body of tissue-equivalent material encompassing the exposure object, which is fixedly connected with the pivot mounting of the X-ray measuring arrangement, whose extent in the direction of the scanning movement is equal to or larger than the scanning lift, and which possesses an electric contouring body resting opposite the rotary compensating body, and which is closely located against the surface of the exposure object after the introduction of the latter into the compensating body.

DISCUSSION OF THE PRIOR ART

A tomographic X-ray apparatus of the above-mentioned type is described in the publication "The British Journal of Radiology" Volume 46, Number 552, 1973, under the title "Computerized Transverse Axial Scanning" (Tomography): Part I, Description of System, pages 1016 through 1022. The holding installation for the exposure object which is utilized in this apparatus possesses a box-shaped compensating body with an elastic front side in the form of a rubber contouring body, which is so shaped that it possesses a recess extending into the interior of the compensating body, in which there may be introduced the exposure object. After the introduction of the exposure object, the compensating body is filled with water so that the contouring body applies itself against the surface of the exposure object. After completion of the exposure, the water is removed so that the exposure object may be withdrawn from the contouring body. The disadvantage of this arrangement, above all, is to be seen in that the contouring body must remain at rest with respect to the compensating body which is fixedly connected with the pivot mounting. Thus, a water-tight rotary connection must be provided between the contouring body and the box or compensating body, which leads to sealing problems. Moreover, the exposure object is constantly subjected to an axial counter pressure corresponding to the water pressure present in the box.

SUMMARY OF THE INVENTION

In order to avoid these disadvantages and to be able, in particular, to introduce the exposure object up to the desired depth into the holding installation without pressure exertion, herewith there is inventively proposed the provision of a compensating body which is constituted of a rigid plastic material of tissue-equivalent density, possessing a cylindrical recess extending symmetrically to the rotational axis of the pivot mounting, which receives the contouring body in the form of a ring having a shape closely contoured to the recess in the compensating body and being slidable therein, and which is of rigid plastic material having a tissue-equivalent density, to the inner side there is fastened an elastic hose which is expandable through a known operative pumping in of water by means of a controllable pumping arrangement. Hereby is achieved that the patient may be introduced into the normally opened recess of the compensating body without axial pressure exertion, and secured in the introduced position through pumping in of water into the elastic hose. In this manner there is achieved that, through the sliding connection of two rigid bodies, there cannot be produced any kind of sealing problems.

In a further construction of the invention it is proposed that the pumping arrangement be formed of a pressure receptacle connected to and located below the hose, which is filled with water and air-tightly sealed on all sides thereof up to apertures for connecting conduits to the hose and for an overflow receptacle similarly located below the hose, in the interior of the pressure receptacle there being located a displacement body expandable through the pumping in of pressurized air and which is in connection with a controllable compressor; and an overflow conduit being located at the highest point of the hose there is an overflow conduit which is connected with the overflow receptacle through a flow or gate valve, the overflow receptacle itself being connected to the pressure receptacle through an outflow conduit which may be closed off by means of a shutoff valve; and including a control installation which, during the operative period of the pumping arrangement, closes the normally open shutoff valve and opens the normally closed flow valve until the attainment of a selectable water level condition in the overflow receptacle. By means of this specialized arrangement including the overflow receptacle there is achieved that air bubbles, unavoidably occur in a closed fluid system with the passage of time, and which are thereby particularly uncomfortable since they lead to the appearance of artifacts or unnatural appearances in the tissues, may be eliminated.

A particularly simple embodiment of the pumping arrangement is derived from the recognition that, in a open hydraulic system with a closed water flow circuit, eventually the air which has entrained in the water may be rapidly separated through a permanent revolving or circulating of the water. Emanating therefrom, in a particular advantageous embodiment, the pumping arrangement is constructed from an open, water-filled supply receptacle, including a liquid pump, which is located below the hose, having an outlet which is connected with the hose through the infeed circuit, as well as a return flow conduit with an adjustable pressure valve which connects into the supply receptacle below the liquid level and connects the latter with the highest point of the hose; and including a switch device for actuation of the pump during the entire period of the tomographic X-raying procedure. Through the constant circulation of the water, any eventually present air bubbles are rapidly conveyed into the supply receptacle and are separated herein.

In order to afford an assured application of the hose against the exposure object, it is desired to attain the highest possible contact pressure. It has hereby been indicated that the maximum pressure exerted on different exposure objects, for example, on the skull of an adult in contrast with that on the skull of an infant, cannot be of equal magnitude. The pressure differences are, however, relatively small and require a highly sensitive control mechanism. As particularly advantageous has been found to be a solution, according to a further feature of the invention, whereby an electromotor is employed as the drive motor for the fluid pump, whose rotational speed is selectable in conformance with the pressure which is permissible for the current exposure object with the aid of an adjusting element.

For extensively different diameters of the exposure objects there the danger is present in that, in the case of a small object diameter, the hose may form folds or creases along the inner surface thereof which would become visible as artifacts in the X-ray image. In a further construction of the invention the foregoing is avoided, in that the inner diameter of the hose, in the unpressurized condition thereof, is equal to the diameter of the smallest exposure object.

It has also been ascertained that during the application on human bodies, in particular in the region of the skull, any temperature deviation between the pressure exerting water and the skin surface is found to be uncomfortable. In a further construction of the invention, there is accordingly provided a thermostatically-regulated heating arrangement for regulating the temperature of the water conducted which is conducted through the hose to approximately body temperature.

BRIEF DESCRIPTION OF THE DRAWINGS

Reference may now be had to the following detailed description of exemplary embodiments of the invention, taken in conjunction with the accompanying drawings; in which.

DETAILED DESCRIPTION

Figure 1:
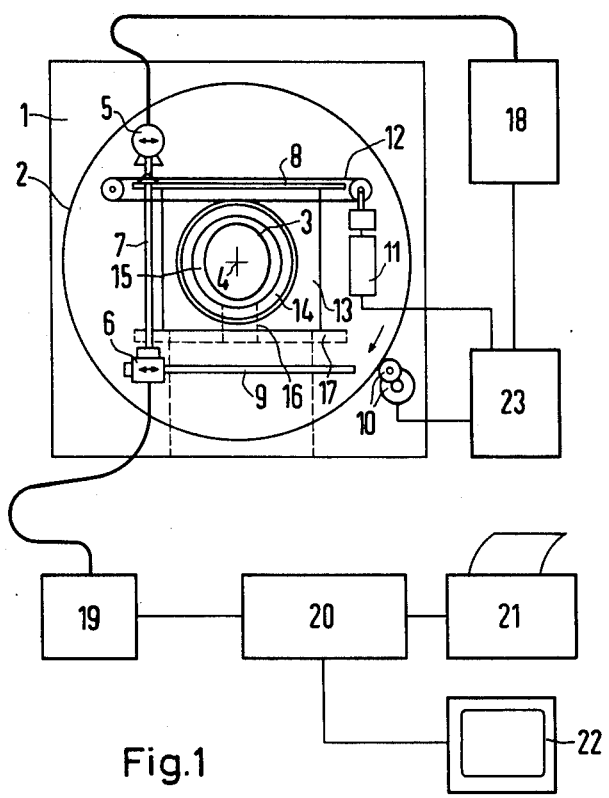
FIG. 1 illustrates a basic schematic arrangement of the tomographic X-ray apparatus constructed pursuant to the invention.

Referring now to the drawings, in the apparatus illustrated in FIG. 1, rotatably supported on a frame portion 1 is a pivot mounting or bogie in the form of a carrier ring 2 so as to be rotatable about an axis 4 coinciding with the middle point of an object 3 which is to be tomographically X-rayed. Located on the carrier ring 2 is an X-ray measuring arrangement, consisting of an X-ray tube 5 and a radiation receiver 6 which are fastened on a connecting rod 7 so as to face each other, and located on guide rails 8 and 9 for linear movement in a direction extending perpendicular to the central beam of the X-ray tube 5. The rotational movement of the carrier ring 2 about the rotary axis 4 is produced by a drive installation 10. A further drive installation 11, with the aid of a cable line 12, effectuates the linear scanning movement of the X-ray measuring arrangement 5, 6 and 7. In addition, fixedly connected with the carrier ring 2 is a rectangular or box-shaped compensating body 13 which is formed of a rigid plastic material having a tissue-equivalent density, for example, acrylic glass. This compensating body possesses a cylindrical recess extending symmetrical to the rotary axis, into which there is inserted in closely-fitted and slidable relationship a contouring body in a form of a ring 14 which, similarly, is constituted of a rigid plastic material having a tissue-equivalent density. Fastened to the inside of the ring 14 is a hose 15 which is constituted of an elastic material. This hose may be filled with water with the aid of a pumping arrangement, to be described in further detail hereinbelow, so that it will fixedly position itself against the outside of the exposure object 3 at a selectable pressure. The ring 14 is rigidly connected with a support table 17 by means of a strap or bracket 16 so that, notwithstanding the rotational movement of the compensating body 13, no rotary torque or turning moment is, imparted to the exposure object 3 resting on the support table 17. The X-ray tube 5 is connected with an X-ray generator 18, which provides it with constant electrical voltage of selective magnitude. The radiation receiver 6 is connected with a computer 20 through the intermediary of a circuit arrangement 19, which will then transmit the data computed therein to a sheet recorder 21, or also to a data viewing apparatus 22 for documentation of, respectively, visual evaluation. The drive installations 10 for the circular movement, and 11, 12 for the linear movement, are connected with a control installation 23 which controls the two movements in accordance with the hereinbelow described kinematic principle.

After the actuation of the apparatus through suitable means (not shown), the control installation 23 at first actuates the drive installation 10 which conveys the carrier ring into an initial position which is offset by 90° with respect to the illustrated location. After reaching this position, there then commences the scanning of the exposure object 3 in a manner whereby the drive installation 11, 12 displaces the measuring arrangement 5, 6, 7 in a linear scan movement in which the desired transverse axial layer of the object 3 is irradiated with the aid of a narrowly focused X-ray whose diameter generally corresponds to the layer thickness, and is concurrently scanned. At the same time, the radiation which passes through the exposure object is measured by the measuring arrangement 6, and is fed into the computer 6 through the circuit arrangement 19, and initially stored therein. The measuring arrangement 6 is so scanned by the circuit arrangement 19 during each scan movement whereby, during this movement, approximately 100 individual values are obtained and fed into the computer 20. After completion of the first scan movement, the control installation then actuates the drive installation 10, which rotates the carrier ring 2 through an angle of about 2°. Thereafter, the control installation again places the drive installation into motion in a reverse direction so that a second scan sequence can be carried out. After completion thereof, the control installation 23 again actuates the drive installation 10 so that the carrier ring 2 once again rotates through an angle of about 2°. Subsequently, the control installation 23 again actuates the drive installation 11, 12 so as to effect a third scan sequence. This procedure repeats itself for about 90 times. During the course of these scanning movements the computer calculates, on the basis of the approximately 9,000 measured values which have been introduced therein, a picture of the irradiated layer, which consists of a matrix having 6,400 points. This picture then appears either in digital form on the sheet recorder 21 or as a "darkening image" on the data viewing apparatus 22.

Figure 2:
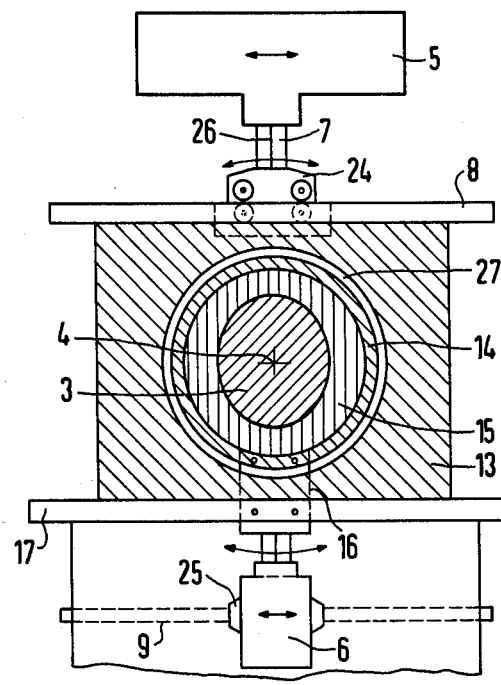
FIG. 2 illustrates a detail elucidating the operating principle of the exposure object holding installation.

Illustrated in FIG. 2 on an enlarged scale is the X-ray measuring arrangement 5, 6, 7 with the object holding installation 13, 14, 15. Therein may be again recognized that the measuring installation, consisting of the X-ray tube 5, the radiation receiver 6, and the connector rod 7, is fastened in the rails 8 and 9 with the aid of carriages 24, 25 so as to be moveable transversely of the central beam 26 of the X-ray tube 5. Located within the cylindrical recess in the compensating body 13, separated by an air gap 27, is the ring 14 in a form-fitting slidable relationship therewith. The hose 15 is fastened to the inside of the ring 14. In order to achieve that the hose 15 rigidly encompasses the exposure object 3 under pressure, after the introduction of the exposure object into the interior of the ring 14, the hose 15 is filled with water through the intermediary of a pump installation, to be described in further detail hereinbelow, and maintained under predetermined pressure.

The basic shape of the hose 15, meaning the shape thereof in an unpressurized condition, is so selected that its inner diameter approximately possesses the magnitude of the diameter of the smallest exposure object. This will afford the hose locating itself without folds or creases against the object. In order to achieve that the opening of the hose 15 attains the largest possible diameter for introduction and withdrawal of the exposure object therethrough, the water supply receptacle of the pumping arrangement is located below the hose 15 so that, upon flow off of the water, there is created a vacuum or subpressure in the hose which has the result in that the hose will locate itself against the inner wall of the ring 14.

Figure 3:
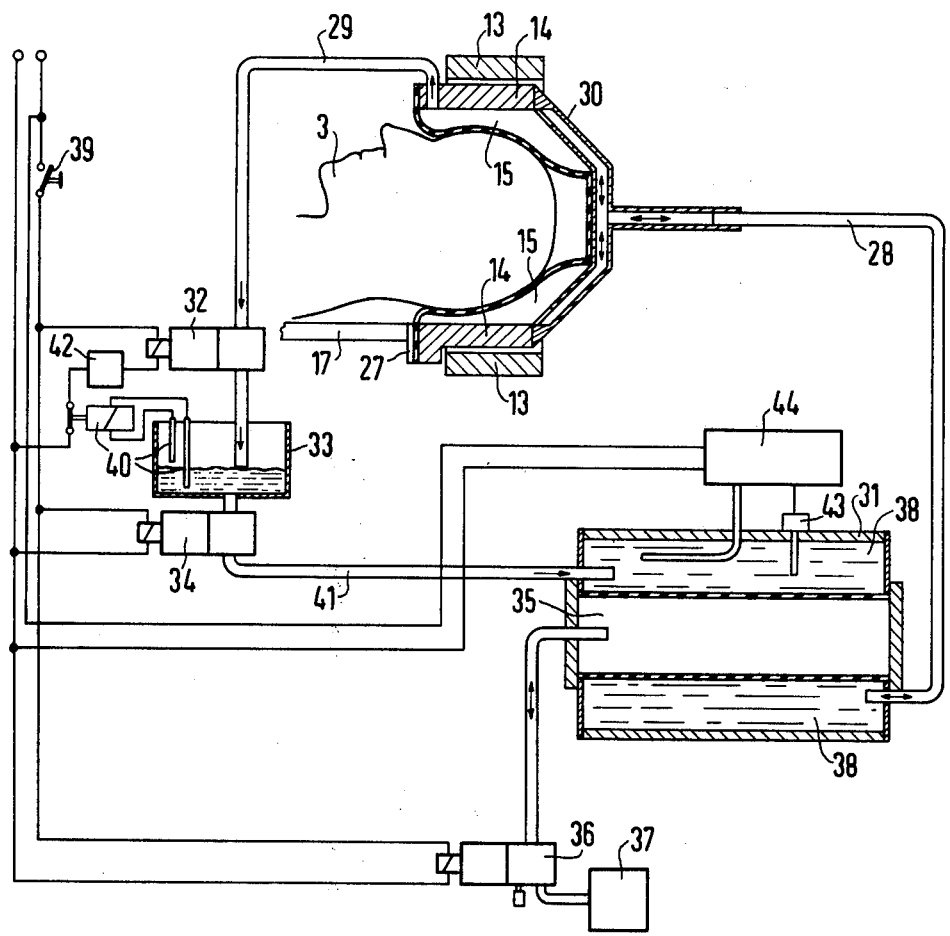
FIG. 3 schematically illustrates a pumping arrangement providing for indirect pressure generation.

Diagrammatically illustrated in FIG. 3 is such an above-mentioned pumping installation. The holding installation, which is shown in cross-section, consists of the compensating body 13, the ring 14 and the hose 15 which encompasses the object 3, and is connected by means of a main water conduit 28 and an overflow conduit 29 with the pumping installation, which is to be described further hereinbelow. The main water conduit 28 is hereby conducted through a conically-shaped support installation 30 which is connected with the ring 14, and connects there at suitable locations with the interior of the hose 15. In contrast therewith, for connection of the overflow conduit 29 it is essential that the connection be carried out at the possibly highest-located point of the hose 15. This is important, since through this conduit any eventually present air bubbles are to be removed from the hose.

The pump installation in itself consists essentially of a water receptacle 31 which is closed on all sides thereof and located below the hose 15, into which there is directly introduced the main water conduit, and the overflow conduit indirectly through a flow valve 32, an overflow tank 33 and a shutoff valve 34. Located interiorly of the water receptacle 31 is an expansible air chamber 35 which is connected to an air pressure generator 37 through a control valve 36.

Preceding the actuation of the pumping arrangement, the entire water supply is located in the water chamber 38 of the water receptacle 31. The subpressure which hereby reigns in the hose 15 causes the object holding installation to be opened to the maximum extent, and the object 3 may thus be comfortably introduced and brought into the desired position. The pumping arrangement is then switched in through actuation of the switch 39. Thereby, the normally closed control valve 36 is opened, the normally opened shutoff valve 34 is closed, and the normally closed flow valve 32 is prepared for opening. Consequently, pressure air flows into the air chamber 35 of the water receptacle 31 and displaces water from the water chamber 38, which then flows into the hose 15 through the main water conduit 28, and gradually fills the hose. After the filling of the hose 15, the flow valve 32 is opened with the aid of a delay element 42 so that the water can flow through the overflow conduit 29 into the overflow tank 33. Since the overflow conduit 29 connects in at the highest point of the hose 15, concurrently conveyed away are any air bubbles which may be present. The overflow tank 33 incorporates a fill-condition indicator 40 which will close the flow valve 32 when a predetermined filling degree has been reached in this tank. After the closure of the flow valve 32, there is produced in the hose 15 a pressure which is generated by the air pressure generator 37, so that the hose 15 on all sides thereof will rigidly lie against the exposure object 3. Thereupon, the tomographic X-ray exposure sequence may now commence. After completion of the tomographic X-raying sequence, or upon termination or failure of the current, there is obtained the following operating cycle:

The control valve 36 closes, whereupon the air escapes from the air chamber 35 of the receptacle 31 and the water flows back under the force of gravity from the hose 15 through the main water conduit 28 into the water chamber 38 of the receptacle 31; the closure valve 34 opens so that the water flows back from the overflow tank 33 through the connecting conduit 41 into the water chamber 38; and the flow valve 32 closes so that a sub-pressure is produced in hose 15 which has the result that at a sufficient differential with respect to the water receptacle 31, the hose will locate itself against the ring 14.

It has been shown that, above all, in use on the human body, and in this instance in the region of the skull, as found to be particularly uncomfortable when the water contained in the hose 15 evidences a temperature which deviates from the body temperature. Due to this reason, the water receptacle 31 contains a heating device 44 which is regulated by a thermostat 43 to body temperature.

Figure 4:
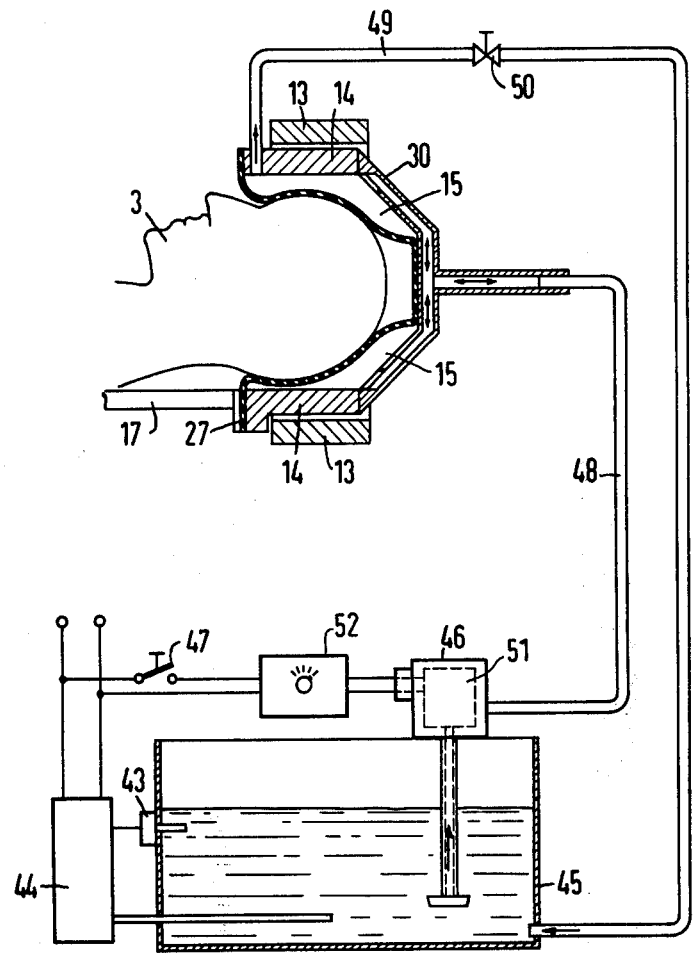
FIG. 4 schematically illustrates a pumping installation providing for direct pressure generation during the circuit flow sequence.

A further and particularly simple embodiment of pumping arrangement is illustrated in FIG. 4. The illustrated object holding installations corresponds to that shown in FIG. 3. In order to distinguish from the pumping arrangement of FIG. 3, in the present one according to FIG. 4 it is, however, not necessary to use either an air pressure generator or an overflow tank, in contrast therewith the installation according to FIG. 4 merely possesses a water receptacle 45, in which there is inserted a dip or immersion pump 46. With the aid of this pump, the water is pumped into the hose 15 through the infeed conduit 48, after actuation through the switch 47 and, after the filling of the hose, flows back through the return flow conduit 49 and a pressure adjusting element 50 into the supply receptacle 45. The switch 47 is closed during the entire tomographic X-ray exposure sequence, so that the described water flow circuit is maintained during the tomographic X-raying. Through intermediary of the pressure adjusting element 50 the desired pressure is hereby constantly maintained in the hose 15. As in the pumping arrangement according to FIG. 3, the one described in FIG. 4 also possesses a thermostatically controlled heating arrangement 43, 44 for the reasons mentioned hereinabove. After completion of the tomographic X-raying procedure, the switch 47 is then opened so that the water which is located in the hose 15 may flow back into the lower positioned water receptacle 45 under the effects of gravity. Through the subpressure which is hereby produced in the hose 15, the latter locates itself against the ring 14 so that the opening attains its maximum size.

In order to correlate the pressure formed in the hose with the current exposure object, the rotational speed of the electromotor which drives the dip or immersion pump 46 may be selected by means of an adjusting element 52.

While there has been shown what is considered to be the preferred embodiment of the invention, it will be obvious that modifications may be made which come within the scope of the disclosure of the specification.

What is claimed is:

1. In a tomographic X-ray apparatus for producing tomographic images of an exposure object, including an X-ray measuring arrangement having an X-ray source generating an X-ray beam for transilluminating said exposure object, whose cross-sectional spread perpendicular to the X-rayed layer is equal to the layer thickness and in parallel with the layer is equal to or lesser than said layer thickness, and an X-radiation receiver for measuring radiation intensity behind said object at successive equidistant points; drive means for said measuring arrangement, said drive means including a pivot mounting for producing rotary movements of said X-ray measuring arrangement through small equidistant angular increments about a rotational axis generally coincident with the symmetrical longitudinal axis of said exposure object, a slide carriage mounted on said pivot mounting for imparting a linear scanning movement to said X-ray measuring arrangement peripendicular to the direction of said X-ray beam across the expanse of said object in alternative sequence with each said incremental angular movement; and holding means for said exposure object in the path of said X-rays including a box-shaped compensating member of tissue-equivalent material fixedly connected with said pivot mounting and encompassing said exposure object, said compensating member being homogeneous and uniformly absorbent in the X-ray direction and having an extent in the direction of scan movement equal to or larger than the scan movement, and an elastic contouring member resting opposite said compensating member adapted to rigidly lie against said exposure object upon the introduction of the latter into said compensating member, the improvement comprising: said compensating member being constituted of a rigid plastic material of tissue-equivalent density; a cylindrical recess in said compensating member extending symmetrically to the rotational axis of said pivot mounting; said contouring member including a rigid plastic material ring of tissue-equivalent material slidably located in said recess in closely-ftted relationship therewith; an elastically expandable hose being fastened to the inner side of said ring; and controllable pumping means being connected to said hose for pumping water thereinto for positioning said hose against said exposure object, said compensating member and said ring of tissue-equivalent material being permeated by the X-ray beam from said X-ray source, said pumping means comprising an airtight, water-filled pressure receptacle connected to and located below said hose, an overflow receptacle connected to and located below said hose, said pressure receptacle including a displacement member interiorly thereof expandable through pumping in of pressurized air, an air pressure generator connected with said displacement member through a control valve, an overflow conduit connected to the highest point of said hose, a flow valve connecting said overflow conduit with said overflow receptacle, a flow-off conduit connecting said overflow receptacle with said pressure receptacle, a shutoff valve in said flow-off conduit, a switch for opening said control valve and flow valve during actuation of said pumping means and concurrently closing said shutoff valve, a level switch in said overflow receptacle for closing said flow valve upon reaching of a selected water level in said overflow receptacle, and a delay element being operatively associated with said flow valve for delaying closure thereof during water return outflow from said hose.

2. A tomographic X-ray apparatus as claimed in claim 1, said hose having an inner diameter in the pressureless condition of said hose equal to the diameter of the smallest exposure object.

3. A tomographic X-ray apparatus as claimed in claim 1, comprising a thermostatically controlled heating arrangement for raising the temperature of the water conducted into said hose to approximately body temperature.

* * * * *